United States Patent [19]

Kirk

[11] 4,361,956
[45] Dec. 7, 1982

[54] OSCILLATING SAW ACCESSORY

[76] Inventor: Norbert A. Kirk, c/o ABC Toy Designers, 43 E. Ohio St., Rm. 930, Chicago, Ill. 60611

[21] Appl. No.: 225,050

[22] Filed: Jan. 14, 1981

[51] Int. Cl.³ .............................................. B27B 9/00
[52] U.S. Cl. .................................. 30/122; 30/166 R; 30/392
[58] Field of Search .................... 30/122, 166 R, 124, 30/133, 392, 123, 388

[56] References Cited

U.S. PATENT DOCUMENTS 2,427,580  9/1947  Stryker ................................ 30/392
3,373,779  3/1968  Taft .................................... 30/122
3,938,251  2/1976  Kareman ............................. 30/124
3,975,821  8/1976  Flicker ................................ 30/133
4,090,297  5/1978  Wanner ............................... 30/124

Primary Examiner—Jimmy C. Peters
Attorney, Agent, or Firm—Larson and Taylor

[57] ABSTRACT

An oscillating saw accessory for a tool having a reciprocating member such as a saber saw is provided. A circular saw blade is mounted in a housing which permits rotary movement of the saw blade. The housing is attached to the tool with the saw blade adjacent to the reciprocating member. The reciprocating member is attached to the saw blade so that the reciprocating movement of the reciprocating member produces an oscillating movement of the saw blade.

10 Claims, 4 Drawing Figures

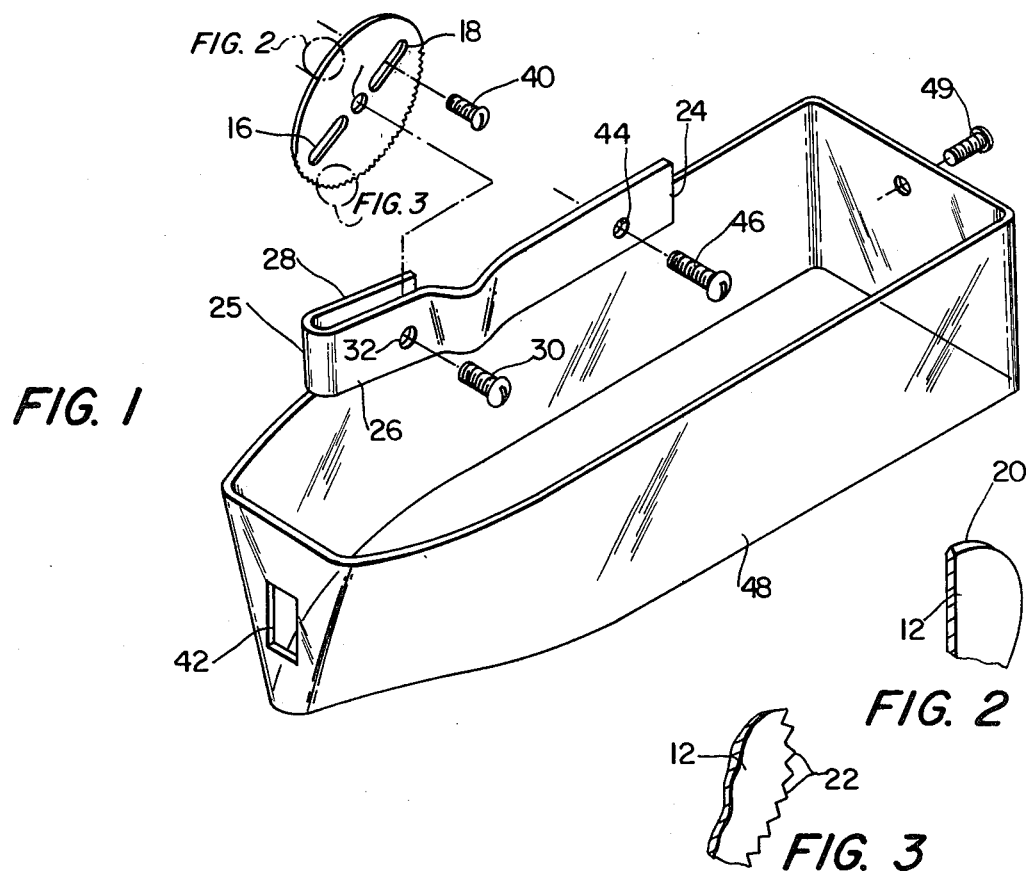
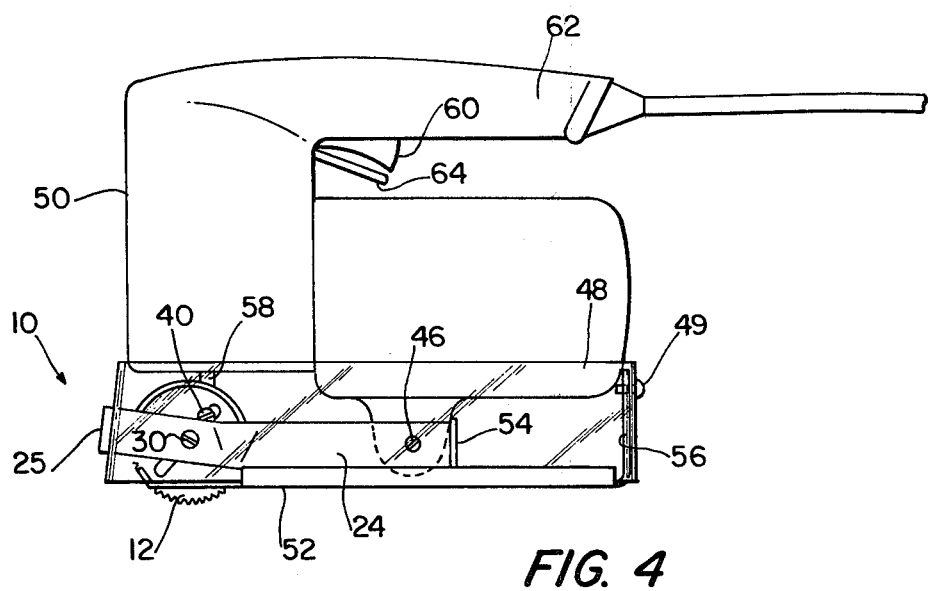

OSCILLATING SAW ACCESSORY

FIELD OF THE INVENTION

This invention relates generally to an accessory for a power tool which provides rotary movement of a saw blade and more particularly to an accessory for a tool having a reciprocating member which produces an oscillating movement of a saw blade.

BACKGROUND OF THE INVENTION

A number of accessories for hand tools in the prior art have been disclosed to provide rotary movement of a circular saw blade. Typical of these prior art devices is the accessory for a drill disclosed in U.S. Pat. No. 1,806,582 to Beutner. In this patent, the rotary movement of the drill is directly coupled to provide rotary movement of a circular saw blade.

There has also been disclosed in the prior art a number of devices for converting rotary movement of a tool to a reciprocating movement. For example, in U.S. Pat. No. 2,822,005 to Lee et al, the rotary movement of a hand drill is converted to an up and down movement of a jig saw blade. Other patents which disclose the similar conversion of rotary movement to reciprocating blade movement are disclosed in the following U.S. Pat. Nos.: 2,783,790 to Keesling; 2,881,519 to Gardner; and 3,266,534 to Carnesecca et al.

While the accessories disclosed in the prior art may be suitable for providing a tool having a rotary movement and a reciprocating movement none of these devices are suitable for transforming the reciprocating movement of a tool to the rotary movement of a circular saw blade.

SUMMARY OF THE INVENTION

In accordance with the present invention, an oscillating saw accessory which is attached to a tool having a reciprocating member is provided. The accessory includes a circular saw blade which is mounted in a housing such that the saw blade can rotate. The housing is attached to the tool so that the saw blade is adjacent to the reciprocating member. The reciprocating member is then connected to the saw blade so that the reciprocating movement of the reciprocating member produces an oscillating movement of the saw blade. The oscillating movement of the saw blade is then used for cutting.

According to a preferred embodiment, the tool is a saber saw and a dust cover surrounds and helps support the housing. The connection between the circular saw blade and the reciprocating member is provided by a cross member which is slidably received in a radial slot in the circular saw blade. If desired, the circular saw blade is reversible so that either a peripheral portion of the saw blade having saw teeth or a peripheral portion of the saw blade having a sharpened edge provides the cutting action.

It should be noted that in the preferred embodiment, the circular saw blade projects below the movable guide of the saber saw. As the movable guide can be rotated to provide a surface at an angle with the circular saw blade, bevel cuts can be made easily with the present invention. In addition, as the circular saw blade only projects a set distance below the guide, dadoing is also easily performed. It should also be noted that the motion of the circular saw blade is oscillatory, rather than rotary. Thus, there is less tendency for the cut material to fly violently away from the saw blade. Of course, the dust cover also helps prevent the flying away of cut material.

Other features and advantages of the present invention are stated in or apparent from the detailed description of a presently preferred embodiment of the invention found hereinbelow.

BRIEF DESCRIPTION OF THE DRAWINGS

FIG. 1 is an exploded perspective view of the oscillating saw accessory of the present invention.

FIG. 2 is an enlarged perspective view of a portion of the circular saw blade depicted in FIG. 1.

FIG. 3 is an enlarged perspective view of another portion of the circular saw blade and depicted in FIG. 1.

FIG. 4 is a plan view of the oscillating saw accessory of the present invention mounted to a saber saw.

DETAILED DESCRIPTION OF THE PREFERRED EMBODIMENT

With reference now to the drawings in which like numerals represent like elements throughout the several views, a presently preferred embodiment of the present invention is depicted in FIG. 1 and comprises an oscillating saw accessory 10 having a circular saw blade 12. Circular saw blade 12 has a central mounting hole 14 and two oppositely located radial slots 16 and 18.

The peripheral edge of circular saw blade 12 is divided into two substantially equal portions. As shown in FIG. 2, one portion of circular saw blade 12 has a sharpened edge 20 along the periphery. The other portion of circular saw blade 12 is depicted in FIG. 3 and shows the peripheral edge having saw teeth 22.

Circular saw blade 12 is mounted in a housing 24 between front flange 26 and rear flange 28. As shown, circular saw blade 12 is mounted on a screw 30 which passes through an aperture 32 in front flange 26, mounting hole 14 of circular saw blade 12, and is received in a threaded hole (not shown) in rear flange 28.

A screw 40 passing through radial slots 18 in saw blade 12 is provided. It should be noted that screw 40 is slidably received in radial slot 18. Housing 24 also has an aperture 44 through which a mounting screw 46 passes. In use, housing 24 is surrounded by a dust cover 48 which is held in place by a screw 49. For convenience, dust cover 48 is made of a transparent material and has an elongate aperture 42 in which the nose 25 of housing 24 is received.

Oscillating saw accessory 10 is depicted in FIG. 4 attached to a saber saw 50. A suitable saber saw for this purpose is a ⅝ inch stroke variable speed Sears Craftsman saber saw, Model No. 315-10700. Saber saw 50 has a variable speed finger switch 60 located on the underside of a handle 62. Located just below finger switch 60 is a finger bar 64. Finger bar 64 acts to prevent the accidental depression of finger switch 60 into handle 62 and the actuation of saber saw 50 when saber saw 50 is picked up by handle 62.

Saber saw 50 is equipped with a guard 52 which is pivotably attached to saber saw 50 by flanges 54 and 56. Housing 24 is attached to the body of saber saw 50 by mounting screw 46. Circular saw blade 12 is connected to reciprocating member 58 of saber saw 50 by screw 40. Conveniently, screw 40 is threadably received by one of the threaded holes which is found in the chuck (not shown) located near the end of reciprocating member 58. Alternatively, a separate threaded hole may be provided in reciprocating member 58. Surrounding housing 24 and portions of saber saw 50 is dust cover 48 which rests on guard 52 and is attached to saber saw 50 by screw 49. As shown, nose 25 of housing 24 is received and mounted in elongate aperture 42.

In operation, oscillating saw accessory 10 functions in the following manner. Initially, the pointed saw blade attached to saber saw 50 is removed from the chuck located at the end of reciprocating member 58. If screw 40 is to be received in this chuck, the screw previously holding this pointed saw blade is removed from the chuck. Next, with circular saw blade 12 already mounted in housing 24 by screw 30, housing 24 is attached to the body of saber saw 50 by mounting screw 46. Depending upon which portion of circular saw blade 12 is to be used, that is the sharpened edge 20 or the saw teeth 22, circular saw blade 12 is rotated to bring either radial slots 16 or 18 adjacent to reciprocating member 58. Then, screw 40 is inserted through radial slot 16 or 18 and attached to reciprocating member 58. Dust cover 48 is then attached to saber saw 50 by screw 49 about housing 24 with nose 25 located in elongate aperture 42.

In order to move saber saw 50 into position for use, the user normally grasps saber saw 50 by handle 62. Without finger bar 64, finger switch 60 is easily depressed accidentally. By using finger bar 64, the finger of the user engages finger bar 64 rather than finger switch 60 when saber saw 50 is picked up. In order to depress finger switch 60, the end of the finger of the user is curled around finger bar 64 so that the tip of the finger engages finger switch 60. Finger bar 64 is shown located directly below finger switch 60. However, it would also be possible to locate finger bar 64 on either side of the bottom of finger switch 60. For right handers, finger bar 64 should be located on the right side of finger switch 60.

During operation of saber saw 50, reciprocating member 58 moves up and down as indicated by the arrow. This reciprocating or up and down motion of member 58 is transmitted to circular saw blade 12 by screw 40 which acts as a connecting cross member. The up and down motion of reciprocating member 58 produces an oscillating motion of circular saw blade 12 as indicated by the arrow. This oscillating motion occurs about the axis of screw 30 which mounts circular saw blade 12 to housing 24. During cutting or sawing, guard 52 rests against the object being cut so that any flying debris which is not trapped under guard 52 but which passes through guard 52 is trapped inside of dust cover 48. With nose 25 of housing 24 in elongate aperture 42 of dust cover 48, dust cover 48 also helps to hold housing 24 steady during operation.

As circular saw blade 12 projects only a limited distance below guard 52, circular saw blade 12 is easily used for cutting grooves or dadoes in objects. In addition, by making the slot in guard 52 through which circular saw blade 12 projects sufficiently wide, guard 52 can be pivoted relative to circular saw blade 12 so that a beveled or angled cut is easily made. It should be noted that changing the portion of circular saw blade 12 from the portion containing saw teeth 22 to the portion containing sharpened edge 20 is easily performed by removing screw 40 and rotating circular saw blade 12 by 180°. Screw 40 is then reinserted through slot 16 and connected to reciprocating member 58 to complete the changeover. It should also be noted that nose 25 which projects slightly beyond dust cover 48 is used as a cutting guide to determine the position of the cut about to be made by saw blade 12.

When it is desired to have a different depth cut than that provided by circular saw blade 12, different sized circular saw blades can be used in place of circular saw blade 12. By using a saber saw 50 with a variable speed stroke, the rotational speed of circular saw blade 12 is easily varied. In this manner, circular saw blade 12 can easily cut a variety of materials including plaster casts, linoleum, plastic, cardboard, rugs, wood, leather, cloth, and metals. In addition, if a carbon blade is provided, cement and marble can be cut as well. The back and forth motion of circular saw blade 12 is also felt to increase the cutting action of circular saw blade 12.

Although the invention has been described in detail with respect to an exemplary embodiment thereof, it will be understood by those of ordinary skill in the art that variations and modifications may be affected within the scope and spirit of the invention.

I claim:

1. An oscillating saw accessory for attachment to a tool having a reciprocating member comprising:
   a circular saw blade;
   a housing for said saw blade;
   means to mount said saw blade to said housing for rotary movement;
   means to attach said housing to the tool such that said saw blade is disposed adjacent to the reciprocating member and the plane of rotation of said saw blade is substantially parallel to the axis of reciprocation of the reciprocating member; and
   means to connect said saw blade to the reciprocating member whereby the reciprocating movement of the reciprocating member produces an oscillating movement of said saw blade which may be used for cutting.

2. An oscillating saw accessory as claimed in claim 1 wherein the tool is a hand-held saber saw.

3. An oscillating saw accessory as claimed in claim 2 wherein said saber saw has a variable speed adjustment for the reciprocating member.

4. An oscillating saw accessory as claimed in claims 2 or 3 further including a depressible finger switch to activate the hand-held saber saw and a finger bar located adjacent to said finger switch to prevent accidental depression of said finger switch.

5. An oscillating saw accessory as claimed in claims 1 or 2 further including a dust cover which is attachable to said housing.

6. An oscillating saw accessory as claimed in claim 4 wherein said dust cover further includes an elongate slot in which a portion of said housing adjacent said saw blade is received.

7. An oscillating saw accessory as claimed in claim 1 wherein said circular saw blade has a radial slot; and wherein said means to connect includes a crossmember which is slidably received in said radial slot, which extends perpendicular to said saw blade, and which is connected to the reciprocating member.

8. An oscillating saw accessory as claimed in claim 1 wherein the periphery of said circular saw blade has saw teeth along substantially one-half thereof and a sharpened edge along the other half thereof such that said saw blade is reversible in said housing to provide a rotary sawing action in one position and a rotary knife cutting action in the reversed position.

9. An attachment for a saber saw having a reciprocating member and guard comprising:

a circular saw blade having at least one radial slot;
a housing for said saw blade;
means to mount said saw blade to said housing for rotary movement;
means to attach said housing to the body of the saber saw such that said saw blade is disposed adjacent to the reciprocating member of the saber saw and with a portion of said saw blade below the guard, the plane of rotation of saw blade being substantially parallel to the plane of the pointed reciprocating blade normally mounted to the reciprocating member;
a safety cover for said housing; and
means to connect said saw blade to the reciprocating member including a crossmember which is attached to the reciprocating member and slidably received in said radial slot such that the reciprocating movement of the reciprocating member produces an oscillating movement of said circular saw blade.

10. An attachment as claimed in claim 9 wherein said safety cover is transparent and rests on the guard, said safety cover further including an elongate slot in which a nose portion of said housing is mounted.

* * * * *